(12) United States Patent
Tsonton et al.

(10) Patent No.: US 6,656,198 B2
(45) Date of Patent: Dec. 2, 2003

(54) TROCAR WITH REINFORCED OBTURATOR SHAFT

(75) Inventors: Mark Tsonton, Loveland, OH (US); Robert Joseph Hughes, Mason, OH (US); Saleem Qureshi, Canton, MI (US)

(73) Assignee: Ethicon-Endo Surgery, Inc., Cincinnati, OH (US)

( * ) Notice: Subject to any disclaimer, the term of this patent is extended or adjusted under 35 U.S.C. 154(b) by 38 days.

(21) Appl. No.: 09/871,922

(22) Filed: Jun. 1, 2001

(65) Prior Publication Data

US 2002/0183775 A1 Dec. 5, 2002

(51) Int. Cl.[7] ............................................. A61B 17/32
(52) U.S. Cl. ................... 606/167; 604/170.01
(58) Field of Search .................. 606/185, 167, 606/172; 604/164.01–164.09, 164.11, 170.01, 170.02, 264, 158, 272; 600/114, 129, 156

(56) References Cited

U.S. PATENT DOCUMENTS

| | | |
|---|---|---|
| 3,613,684 A | 10/1971 | Sheridan |
| 3,994,287 A | 11/1976 | Turp et al. |
| 5,271,380 A | 12/1993 | Riek et al. |
| 5,334,150 A | 8/1994 | Kaali |
| 5,376,076 A | 12/1994 | Kaali |
| 5,380,291 A | 1/1995 | Kaali |
| 5,389,077 A | 2/1995 | Melinyshyn et al. |
| 5,431,151 A | 7/1995 | Riek et al. |
| 5,551,947 A | 9/1996 | Kaali |
| 5,569,291 A * | 10/1996 | Privitera et al. ............. 606/185 |
| 5,685,820 A | 11/1997 | Riek et al. |
| 5,709,671 A | 1/1998 | Stephens et al. |
| 5,772,660 A * | 6/1998 | Young et al. .......... 604/165.01 |
| 5,797,946 A | 8/1998 | Chin |
| 5,817,061 A * | 10/1998 | Goodwin et al. ........... 600/121 |
| 5,916,233 A | 6/1999 | Chin |
| 5,993,384 A | 11/1999 | Lunsford et al. |
| 6,007,481 A | 12/1999 | Riek et al. |

FOREIGN PATENT DOCUMENTS

| | | |
|---|---|---|
| DE | 4035146 A1 | 5/1992 |
| EP | 484725 B1 | 3/1996 |
| JP | 3288593 A1 | 9/1992 |

* cited by examiner

Primary Examiner—Tejash Patel
(74) Attorney, Agent, or Firm—Dean Garner

(57) ABSTRACT

In accordance with the present invention there is provided an obturator for penetrating body tissue which contains a handle and a shaft. The shaft has a proximal end attached to the handle and a distal end extending from it. The handle and shaft are formed from a single piece of molded polymer. A substantially rigid reinforcing member which is formed from a material having a greater rigidity than the molded polymer is disposed along the shaft.

15 Claims, 4 Drawing Sheets

TROCAR WITH REINFORCED OBTURATOR SHAFT

FIELD OF THE INVENTION

This invention generally relates to surgical instruments; and more particularly, the invention relates to trocar devices for providing communication to the abdominal cavity. Trocar devices in accordance with the present invention include a substantially reinforced obturator shaft which adds rigidity to overcome unwanted deflection during penetration.

BACKGROUND OF THE INVENTION

A trocar is a surgical instrument that is used to gain access to the abdominal cavity. A trocar generally comprises two major components, a cannula and an obturator. In order to penetrate the skin, a small incision is made by the surgeon where the trocar is to be inserted. The distal end of the trocar is then inserted into the tissue. The obturator has a point or cutting edge at its distal end. By applying pressure against the proximal end of the obturator, the point is forced through the tissue until it enters a target location, such as the abdominal cavity. The cannula is inserted through the perforation made by the obturator and the obturator is withdrawn, leaving the cannula as an access to the abdominal cavity.

Because trocars included sharp blades, inadvertent tissue or organ puncture was a concern. One of the first technical challenges in connection with the design and manufacture of the trocar was the incorporation of features to enhance safety. Specifically, it was important to develop a safety trocar which could substantially lessen the possibility of unintentional tissue or organ puncture. A trocar which includes a safety shield on the obturator was developed to lessen the possibility of unintentional puncture. The shield is biased in an extended position to cover the penetrating tip of the obturator. When the surgeon desires to penetrate tissue with the trocar, the safety shield retracts and exposes the penetrating tip. The shield remains in the retracted position so long as pressure is continuously applied. When the surgeon fully punctures the body wall, the pressure is relieved and the safety shield returns to its extended position covering the penetrating tip. Therefore, inadvertent puncture of bodily tissue and organs within the body cavity can be avoided. An example of a trocar having a safety shield is disclosed in U.S. Pat. No. 5,709,671 issued to Stephens et al. on Jan. 20, 1998, which is hereby incorporated herein by reference.

While numerous trocars have been designed to prevent inadvertent puncture, there was still clearly room for improvement. Regardless of the safety mechanisms built into these instruments, there were concerns of accidental puncture to body organs. Therefore, other mechanisms for protecting tissues and organs from inadvertent puncture during surgery were developed. One such development in the design of trocars relates to the incorporation of visualization concurrently with penetration. An example of a patent which discloses a surgical penetration instrument adapted for visualization during penetration is U.S. Pat. No. 5,271,380 issued to Riek, et al. on issued Dec. 21, 1993, which is hereby incorporated herein by reference. This patent describes a penetrating instrument including a hollow, cylindrical sleeve and an imaging element attached to the sleeve at its distal end. In a preferred embodiment, it has a conical non-bladed penetrating tip to facilitate the advancement of the instrument into body tissue. The non-bladed obturator separates rather than cuts tissue while penetrating to gain access to a body cavity. In this way, the incorporation of a safety shield or another mechanism to protect tissue or organs from inadvertent puncture during insertion is unnecessary.

The advancement of the optical non-bladed obturator reduced safety concerns and inadvertent tissue punctures encountered with early trocars; however, there was still opportunity for improvement. The trocars in the prior art are constructed of a large number of elements requiring various techniques in assembling the optical non-bladed obturator, creating manufacturing challenges. For example, manufacturers assemble the obturator by gluing the penetrating tip on the shaft of the obturator, or by using other mechanical means known in the art. Not only is the large number of elements a challenge to assemble, there is also a significant cost associated with assembling all of these elements.

Many of the surgeons using the optical non-bladed obturator began using it without the aid of the imaging device. The surgeons found that they were comfortable performing the surgical procedures using tactile feed back.

This surgical preference and the desire to reduce manufacturing challenges and costs led to the development of a one-piece solid plastic non-bladed obturator. The one-piece solid plastic non-bladed obturator enabled the use of conventional plastic processing methods such as injection molding, thus reducing manufacturing and assembly costs. Using injection molding, the one-piece solid plastic obturator had a straight injected molded plastic shaft. However, tests showed that the force required to penetrate tissue was great enough to cause unwanted deflection of the molded obturator shaft, especially on small diameter devices. This flexibility would be problematic during tissue penetration. This invention overcomes the obturator shaft deflection problem.

SUMMARY OF THE INVENTION

In accordance with the present invention there is provided an obturator for penetrating body tissue which contains a handle and a shaft. The shaft has a proximal end attached to the handle and a distal end extending from it. The handle and shaft are formed from a single piece of molded polymer. A substantially rigid reinforcing member which is formed from a material having a greater rigidity than the molded polymer is disposed along the shaft.

DETAILED DESCRIPTION OF THE PREFERRED EMBODIMENT

Figure 1:
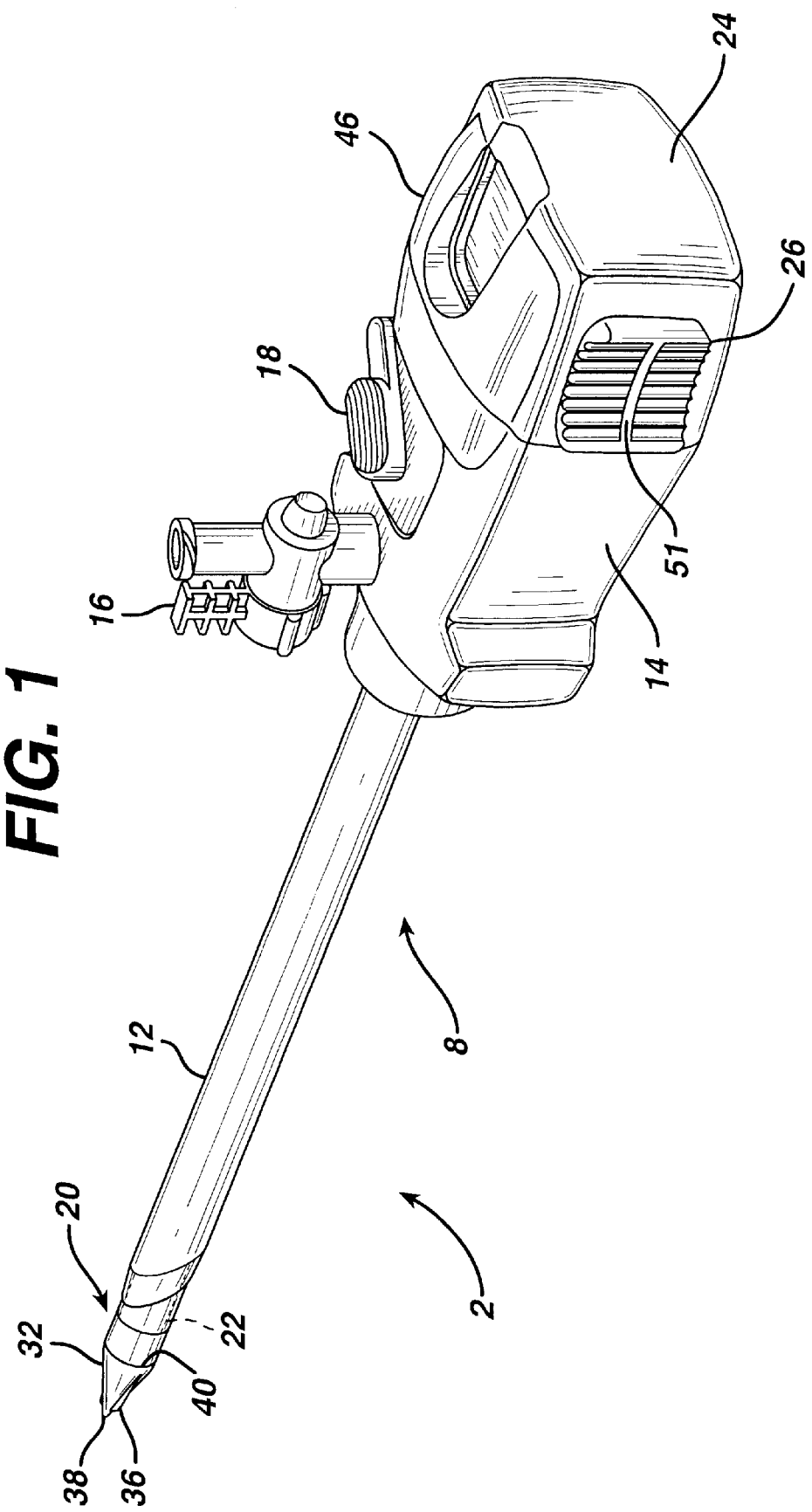
FIG. 1 is a perspective view of a trocar assembly including the obturator of the present invention.

Reference numerals are used in this description to designate the various components and elements of the instrument of this invention. Identical reference numerals designated in the various drawings refer to the identical element or component of the surgical penetration instrument. As used in this description, "proximal" or "proximally" refers to that portion of the instrument, component, or element which extends toward the user. Conversely, "distal" or "distally" refers to that portion of the instrument, component, or element which extends away from the user.

Figure 2:
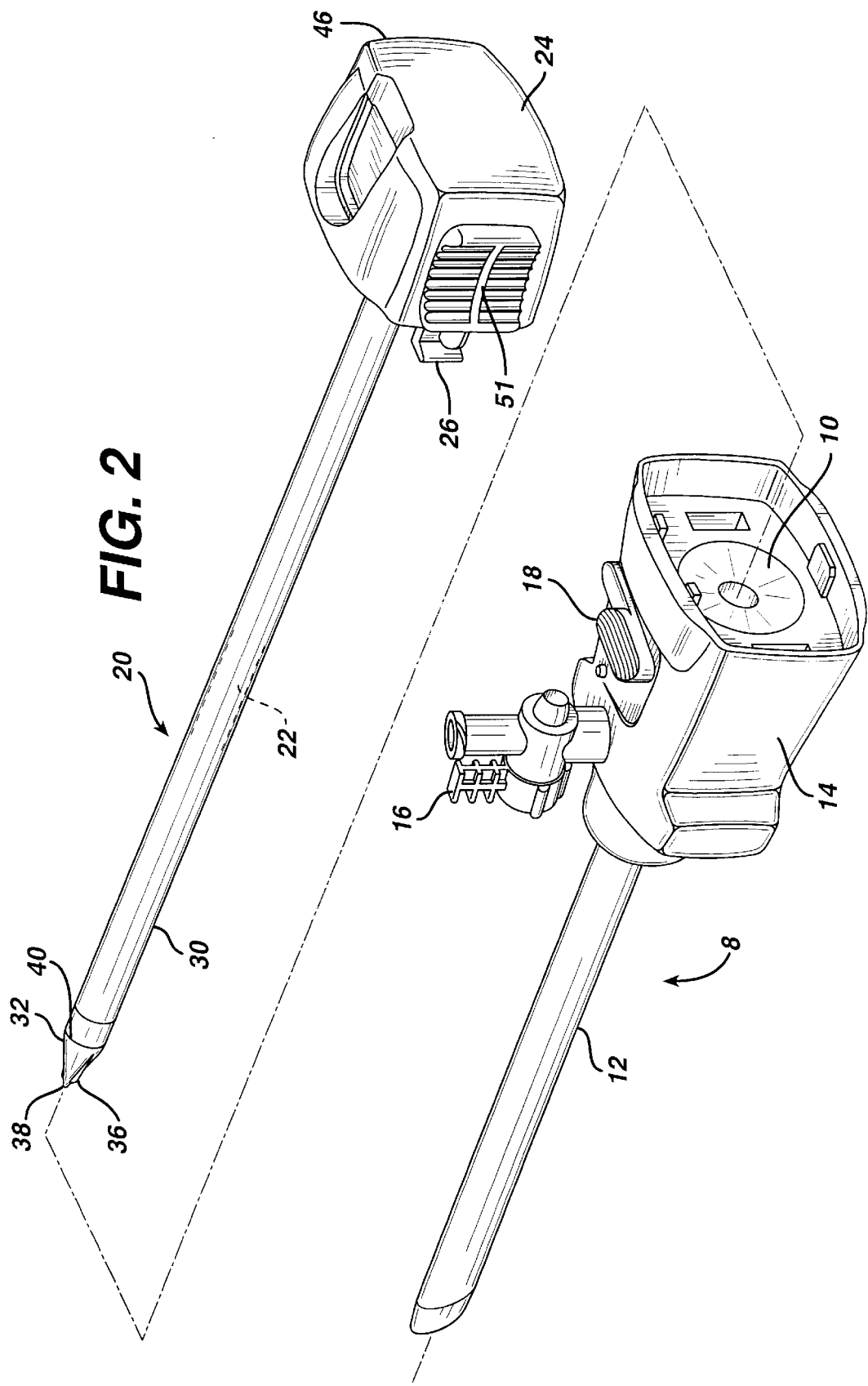
FIG. 2 is an exploded perspective view of the trocar showing the obturator and cannula separated.

Referring to FIGS. 1 and 2, there is shown trocar 2 which incorporates obturator 20 and cannula 8 of the present invention. As illustrated in FIG. 2, obturator 20 is inserted into and through valve 10 and into sleeve housing 14 and sleeve 12. During insertion, an internal valve (not shown) connected to valve lever 18 is opened. Seal 10 is preferably a septum valve which surrounds shaft 22 preventing any fluid or gas from escaping through cannula 8. When shaft 22 is fully inserted into cannula 8, hub 24 is secured to sleeve housing 14 by handle 26. Penetrating tip 32 of obturator 20, and a portion of the distal end of shaft 22, extend distally from sleeve 12.

In an actual surgical procedure utilizing the device of the present invention, a surgeon, using a scalpel, makes a small incision where trocar 2, shown in FIG. 1, is to be positioned during the surgical procedure. The distal end of trocar 2 is then inserted into the tissue exposed by the small incision. After insertion into the tissue, trocar 2 is oscillated back and forth around its axis to facilitate penetration. Separators 34 and 36 on penetrating tip 32 help to separate tissue during oscillation to facilitate the advancement of trocar 2 into the abdominal cavity.

After penetration into the abdominal cavity is complete, obturator 20 is removed from cannula 8 by pressing buttons 51 and 52 (not shown) which releases handle 26 from sleeve housing 14. When obturator 20 is removed an internal valve (not shown) connected to valve lever 18 closes preventing any fluid or gas from escaping cannula 8. If desired, a pressurizing gas such as carbon dioxide can be selectively pumped through sleeve 12 via stopcock 16. Surgical instruments, such as linear staplers, graspers, clip appliers, scopes etc. can now be inserted through cannula 8 to perform a procedure at the surgical site.

Referring again to FIGS. 1 and 2, cannula 8 includes sleeve 12 and sleeve housing 14. Sleeve 12 extends distally from sleeve housing 14. Sleeve housing 14 includes stopcock 16, valve lever 18, and seal 10.

Figure 3:
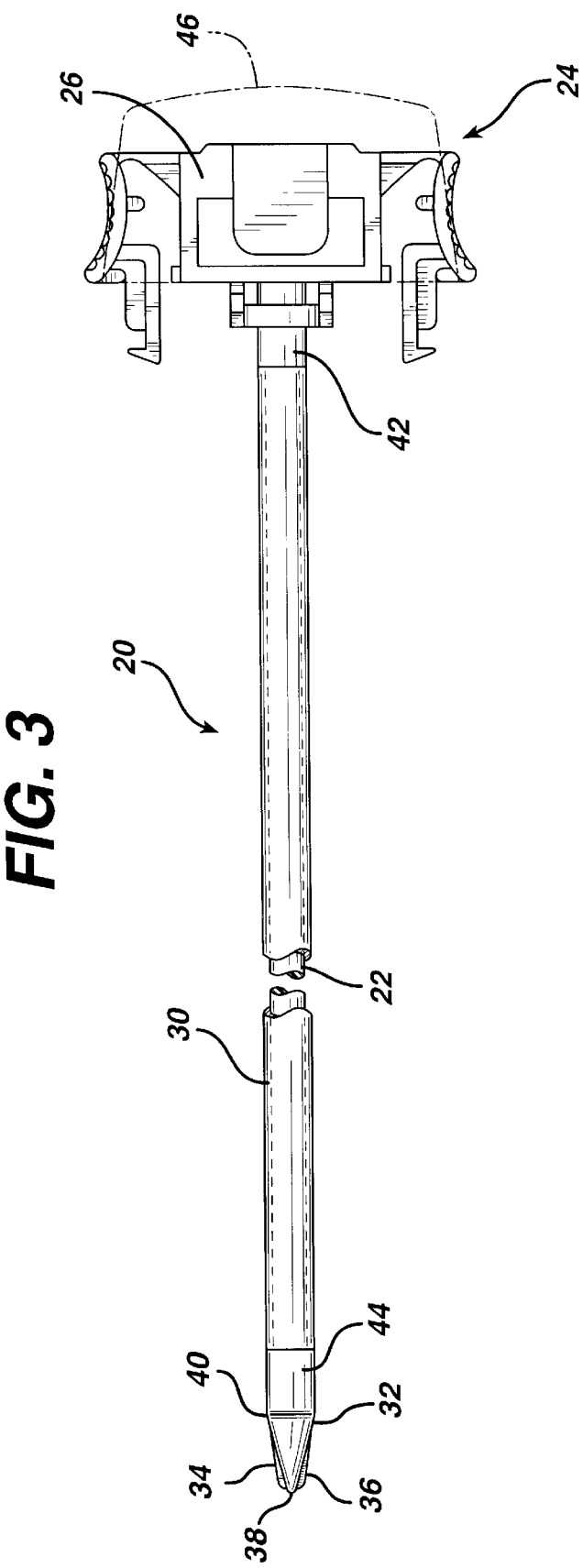
FIG. 3 is a plan view of the obturator of the present invention.

Obturator 20, as shown in FIG. 3, has a shaft 22 having a proximal end 42 attached to handle 26, and a distal end 44 extending therefrom. Handle 26 and shaft 22 are formed from single piece of molded polymer. Shaft 22 preferably includes a conical penetrating tip 32 which is integrally molded to shaft 22 at its distal end 44. Tip 32 includes first and second separators 34 and 36 which extend outwardly from penetrating tip 32. Handle 26 has a cap 46 attached to the proximal end 42 of shaft 22. Cap 46 is snapped onto handle 26 and is secured thereon by an interference fit.

Figure 4:
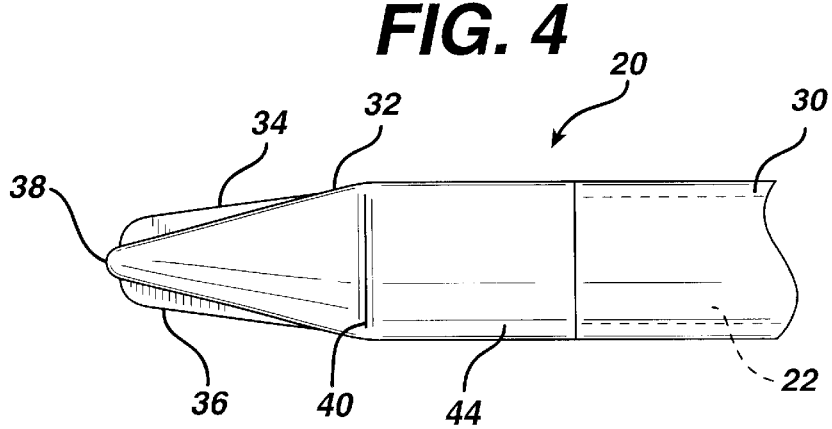
FIG. 4 is an enlarged view of the penetrating tip of the obturator.
Figure 5:
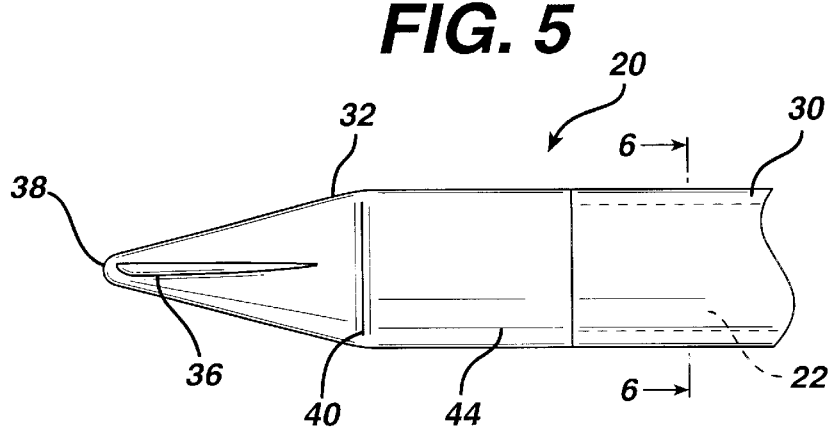
FIG. 5 is an enlarged view of the penetration tip, shown in FIG. 4 rotated 90°.

Referring now to FIGS. 4 and 5, penetrating tip 32 is molded integrally to shaft 22 at distal end 44. Penetrating tip 32 has circular base 40 and blunt point 38 extending distally from base 40. Base 40 is positioned adjacent to the distal end 44 of shaft 22. First and second separators 34 and 36, respectively, have generally straight, linear edge surfaces. Each first and second separator 34 and 36 extends longitudinally from adjacent to base 40 toward point 38 of penetrating tip 32. First and second separators 34 and 36 are spaced about 180° from each other, and are positioned proximally to point 38.

Figure 6:
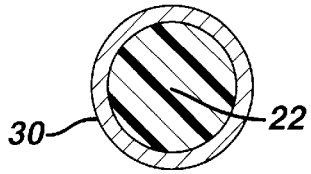
FIG. 6 is a cross-sectional view taken along line 6—6 of FIG. 5 of the preferred embodiment of the reinforced shaft of the obturator in the present invention.

Referring again to FIG. 3, shaft 22 further includes a reinforcing member 30 disposed thereon. In the embodiment illustrated in FIG. 6, member 30 is a rigid reinforcing hollow tube made of stainless steel, titanium or any other suitable material known to those skilled in the art. Using manufacturing methods like injection molding, a polymer such as polycarbonate, or any other suitable polymer known to those skilled in the art, can be injected through member 30 wile forming shaft 22 and handle 26. Other manufacturing methods, readily apparent to those skilled in the art, could also be used to make the present invention.

Figure 7:
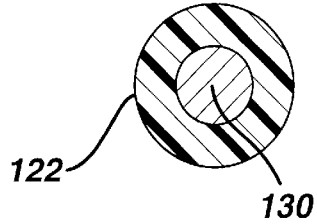
FIG. 7 is a cross-sectional view taken along line 6—6 of FIG. 5 of a second, alternate embodiment of the reinforced shaft of the obturator in the present invention.

An alternate embodiment of the present invention is shown in FIG. 7. In this embodiment, shaft 122, similar to shaft 22, includes a reinforcing member 130 disposed within the shaft 122. Member 130 is a solid cylindrical rod made of a reinforcing material such as stainless steel, aluminum or any other material known to those skilled in the art. Using manufacturing methods like injection molding, shaft 122 and handle 126 (not shown) can be integrally molded as a single piece around member 130.

Figure 8:
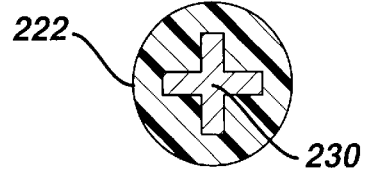
FIG. 8 is a cross-sectional view taken along line 6—6 of FIG. 5 of a third, alternate embodiment of the reinforced shaft of the obturator in the present invention.

FIG. 8 shows another alternate embodiment, similar to that shown in FIG. 7, wherein shaft 222 includes of a member 230 disposed therein. Member 230 is similar to member 130 but has a plus shaped cross-section. As will be appreciated by those skilled in the art, many other suitable cross-sectional configurations other than circular and plus, can be used in the present invention.

Although particular embodiments of the present invention have been shown and described, other embodiments will become apparent to those skilled in the art without departing form the spirit and scope of the present invention. The terms used in describing the invention are used in their descriptive sense and not as terms of limitations.

What is claimed is:

1. An obturator for penetrating body tissue, said obturator comprising:
   a. a handle and a shaft, said shaft having a proximal end attached to said handle, and a distal end extending therefrom, said handle and said shaft formed from single piece of molded polymer; and
   b. a substantially rigid reinforcing member disposed along and fixedly attached to said shaft, said member formed from a material having greater rigidity than said molded polymer, said member is a solid rod embedded within said shaft wherein said rod has a plus shaped cross-section.

2. The obturator according to claim 1, wherein said distal end has a penetrating tip thereon.

3. The obturator according to claim 2, wherein said penetrating tip is generally conical.

4. The obturator according to claim 2, wherein said penetrating tip has at least one separator extending outwardly therefrom.

5. The obturator according to claim 1, wherein said member is a hollow cylindrical tube disposed around said shaft.

6. The obturator according to claim 1, wherein said member comprises a metal.

7. A trocar comprising:
   a. a cannula comprising a tubular sleeve having a proximal end, a distal end and a passageway therethrough, said cannula having a housing attached to said proximal end of said sleeve, said housing having an opening at a proximal end thereof which is in communication with said passageway of said sleeve;

b. an obturator insertable into said cannula, said obturator comprising a handle and a shaft, said shaft having a proximal end attached to said handle and a distal end extending therefrom, said handle and said shaft formed from single piece of molded polymer; and c. a substantially rigid reinforcing member disposed along and fixedly attached to said shaft, said member formed from a material having a greater rigidity than said molded polymer.

8. The obturator according to claim 7, wherein said distal end has a penetrating tip thereon.

9. The obturator according to claim 8, wherein said penetrating tip is generally conical.

10. The obturator according to claim 8, wherein said penetrating tip has at least one separator extending outwardly therefrom.

11. The obturator according to claim 7, wherein said member is a hollow cylindrical tube disposed around said shaft.

12. The obturator according to claim 7, wherein said member is a solid rod embedded within said shaft.

13. The obturator according to claim 12, wherein said rod is cylindrical.

14. The obturator according to claim 12, wherein said rod has a plus shaped cross-section.

15. The obturator according to claim 7, wherein said member comprises a metal.

\* \* \* \* \*